US006205352B1

United States Patent
Carroll

(12) United States Patent
(10) Patent No.: US 6,205,352 B1
(45) Date of Patent: Mar. 20, 2001

(54) SENTINEL NODE IDENTIFICATION USING NON-ISOTOPE MEANS

(75) Inventor: Robert G. Carroll, Largo, FL (US)

(73) Assignee: Oncology Innovations, Inc., Largo, FL (US)

( * ) Notice: Subject to any disclaimer, the term of this patent is extended or adjusted under 35 U.S.C. 154(b) by 0 days.

(21) Appl. No.: 09/195,481

(22) Filed: Nov. 18, 1998

Related U.S. Application Data

(60) Provisional application No. 60/065,491, filed on Nov. 19, 1997.

(51) Int. Cl.$^7$ .......................................................... A61B 5/00
(52) U.S. Cl. ........................... 600/431; 600/437; 600/473; 424/9.3; 424/9.4; 424/9.5; 424/9.6
(58) Field of Search ............................... 60/407, 430, 431, 60/437, 438, 458, 464, 473, 475; 424/9.3, 9.341, 9.351, 9.4, 9.5, 9.6

(56) References Cited

U.S. PATENT DOCUMENTS

| | | |
|---|---|---|
| 5,101,827 | 4/1992 | Goldenberg . |
| 5,260,050 * | 11/1993 | Ranney ..................................... 424/9 |
| 5,383,456 | 1/1995 | Arnold et al. . |
| 5,579,766 | 12/1996 | Gray . |
| 5,582,172 | 12/1996 | Papisov et al. . |
| 5,611,344 | 3/1997 | Bernstein et al. . |
| 5,707,607 | 1/1998 | Quay . |
| 5,732,704 | 3/1998 | Thurston et al. . |
| 5,776,094 | 7/1998 | Goldenberg . |
| 5,807,536 * | 9/1998 | Morcos ................................. 424/9.5 |

OTHER PUBLICATIONS

Gulec, et al., "The Expanding Clinical Role for Intraoperative Gamma Probes," Nuclear Medicine Annual 1997. pp. 209–237.

Kapteijn et al., "Localizing the Sentinel Node in Cutaneous Melanoma: Gamma Probe Detection Versus Blue Dye," Annals of Surgical Oncology, 4(2), 1997, pp. 156–160.

Krag, M.D., et al. "The Sentinel Node in Breast Cancer," The New England Journal of Medicine, No. 14, Oct. 1, 1998. 339:941–946.

Paganelli, Giovanni, "Sentinel node biopsy: role of nuclear medicine in conservative surgery of breast cancer," Eur J Nucl Med, No. 2, Feb. 1998. 25:99–100.

Veronesi et al., "Sentinel–node biopsy to avoid axillary dissection in breast cancer with clinically negative lymph–nodes," Lancet, Jun. 28, 1997. 349:1864–1867.

* cited by examiner

Primary Examiner—William E. Kamm
(74) Attorney, Agent, or Firm—Caesar, Rivise, Bernstein, Cohen & Pokotilow, Ltd.

(57) ABSTRACT

A method for identifying a sentinel node is provided. The method includes injecting tumor-bearing tissue with a marking composition, radiating marking-agent-targeting energy into suspect tissues potentially harboring the sentinel node, and detecting a lymph node within the suspect tissues first infiltrated by the marking agent. The method is conducted without detecting radioactivity, and thus avoids the health and environmental problems posed by methods based on detecting radiolabels. Moreover, the method obviates the need for surgical dissection to initially detect potential sentinel nodes. Also provided are systems for performing the method and compositions for use in the method.

35 Claims, No Drawings

SENTINEL NODE IDENTIFICATION USING NON-ISOTOPE MEANS

CROSS-REFERENCES TO RELATED APPLICATIONS

This application claims priority from provisional U.S. Patent Application No. 60/065,491, filed Nov. 19, 1997.

FIELD OF THE INVENTION

This invention relates to methods, compositions and apparatuses for detecting sentinel nodes, and more particularly to means for transcutaneously identifying sentinel nodes, which do not employ radioactive isotope marking agents.

BACKGROUND OF THE INVENTION

Due to the propensity of malignant tumors to metastasize through the lymphatic system, it has in the past been normal practice in some situations to remove all lymph nodes potentially harboring malignant cells metastasized from a tumor. Recently, the technique of interoperative lymphatic mapping has taken much of the guesswork out of determining which lymph nodes to remove. The at least one lymph node (typically 1–3 lymph nodes) which is the first to receive lymphatic drainage from the tumor (i.e., the sentinel node) is identified and biopsied. If the at least one sentinel node is free of malignant cells, then further lymph node biopsies can be avoided.

Sentinel nodes have been identified by injecting a marking agent into the tumor-bearing tissue and tracing the pathway of the marking agent through the lymphatic system. Visible marking agents have been employed to visually detect sentinel nodes with the naked eye, but such methods typically require significant surgical dissection to view the potential sentinel nodes and detect the presence of marking agent therein. Radioactive isotopes have also been employed as sentinel node marking agents. See, e.g., Kapteijn et al., "Localizing the sentinel node in cutaneous melanoma: gamma probe detection versus blue dye," 4(2) Ann. Surg. Oncol. 156–60 (Mar. 1997) and U.S. Pat. No. 5,732,704 to Thurston et al. These techniques comprise injecting radioactive isotope compositions into the tumor bearing tissue and detecting the migration of the composition from the tumor and into the lymphatic system.

Although such radiochemistry techniques are an improvement over prior visible detection methods in that radioactive marking agents can be detected transcutaneously (regardless of the depth of the sentinel node within the tissue), radiochemistry techniques are less than ideal in a number of aspects. Patients and medical personnel are exposed to potentially harmful doses of ionizing radiation. Radioactive isotopes also pose environmental contamination and disposal issues.

Thus, there has been a need for a method of transcutaneously identifying a sentinel node without using radioactive isotopes.

All references cited herein are incorporated herein by reference in their entireties.

SUMMARY OF THE INVENTION

The invention addresses at least the foregoing deficiencies of the prior art in providing a method for identifying a sentinel node, comprising:

injecting tumor-bearing tissue with a marking composition comprising a marking agent;

radiating marking-agent-targeting energy into suspect tissues potentially harboring said sentinel node; and detecting a lymph node first infiltrated by said marking agent to identify said sentinel node, said detecting being across a substantial thickness of said suspect tissues, wherein said method is conducted without detecting radioactivity.

The invention also provides systems for performing the method of the invention and compositions for use in the method of the invention.

DETAILED DESCRIPTION OF PREFERRED EMBODIMENTS

The invention provides methods and systems for identifying at least one sentinel node across a substantial thickness of tissue without using radioactive isotopes. The methods and systems employ marking agents that enable trans-tissue (e.g., transcutaneous) detection of sentinel nodes via ultrasonic detection, magnetic resonance detection and/or laser-enhanced detection.

The trans-tissue detection methods and systems of the invention do not require surgical dissection to reveal potential sentinel nodes to the naked eye. The invention enables noninvasive detection of sentinel nodes across a substantial thickness of tissue, e.g., substantially below the surface of the skin. A tissue is of substantial thickness if it is thick enough to conceal a dye-infiltrated sentinel node from the naked eye under ambient lighting conditions. Unlike prior art methods employing blue dyes, the invention enables noninvasive detection of sentinel nodes through tissue (including skin) at least 2 mm thick, and even at least 5 mm thick.

Ultrasound Non-imaging/Imaging Signal Transduction

The invention enables ultrasound identification of the first lymph nodes to drain a solid tumor. A marking composition comprising an ultrasound contrast agent is subcutaneously injected adjacent the tumor-bearing tissue and allowed sufficient time to migrate to the sentinel node before detection begins. The marking composition can be, e.g., injected between the skin and the immediately underlying tumor, as suggested by the European Institute of Oncology. See, e.g., Paganelli "Sentinel node biopsy: role of nuclear medicine in conservative surgery of breast cancer." European Journal of Nuclear Medicine 1998, 25: 99–100, and Veronesi et al. Lancet 1997, 349: 1864–67. In the United States, the National Cancer Institute has published studies of a technique whereby 1 ml volumes of lymphatic tracer are injected at 3-,6-,9-, and 12-o'clock positions into the breast surrounding the primary tumor or biopsy cavity. See, e.g., Krag et al., "The Sentinel Node in Breast Cancer, A Multicenter Validation Study." New England Journal of Medicine 1998; 339: 941–946. A broad overview of the intraoperative use of gamma probes is presented in Gulec et al., "The Expanding Clinical Role for Intraoperative Gamma Probes." Nuclear Medicine Annual 1997: 209–237.

The ultrasound marking composition is preferably a pharmaceutically acceptable composition containing an ultrasound contrast agent, preferably coated with a phagocytosis enhancing material, such as tufsin, and a carrier suitable for subcutaneous infection. The ultrasound contrast agent is sufficiently small to migrate from the tumor-bearing tissue to the sentinel node, and is sufficiently stable to survive the trip and remain within the sentinel node long enough to be detected. Ultrasound contrast agents of the invention are preferably about 10 to about 200 nanometers in diameter. In embodiments, the ultrasound contrast agents reflect sound a million-fold more than adjacent soft tissues. Ultrasound contrast agents and pharmaceutically acceptable compositions containing them are generally disclosed in, e.g., U.S. Pat. Nos. 5,707,607 and 5,611,344 and the references cited therein.

In embodiments, a simple non-imaging ultrasound contrast agent detecting tissue penetrable probe is used in conjunction with conventional transcutaneous ultrasound imaging devices to provide probe surgical guidance to and probe confirmation of the identity of the sentinel lymph node in the context of an ultrasound image of the node and adjacent blood vessels.

Penetrable combined tissue imaging and signal intensity measuring ultrasound probes modeled on existing transvaginal imaging probes (some of which incorporate Doppler technology) provide visualization of adjacent anatomical structures, a critical improvement over gamma detecting probes which only indicate the direction in which labeled tissue may be found by careful tissue dissection.

Ultrasound contrast agent detecting probes avoid patient and staff exposure to potentially harmful doses of ionizing radiation. Avoiding radioactive isotopes also avoids environmental contamination and disposal issues.

Ferromagnetic Detection/MRI Non-imaging Signal Transduction

The invention enables simple magnetic or paramagnetic detection or more complex magnetic resonance identification of the first lymph nodes to drain a solid tumor. A marking composition comprising a magnetic or paramagnetic compound, such as a species of gadolinium, iron, manganese, rhenium, europium, lanthanum, holmium, or fermium, is subcutaneously injected adjacent the tumor-bearing tissue and allowed sufficient time to migrate to the sentinel node before detection begins. The marking composition is preferably injected between the skin and the immediately underlying tumor, as suggested by the European Oncology Institute's studies discussed above.

The marking composition is preferably a pharmaceutically acceptable composition containing a magnetic or paramagnetic compound such as a species of gadolinium, iron, manganese, rhenium, europium, lanthanum, holmium, or fermium marking agent, preferably coated with a phagocytosis enhancing material, such as tufsin, and a carrier suitable for subcutaneous injection. The magnetic or paramagnetic marking agent is sufficiently small to migrate from the tumor-bearing tissue to the sentinel node, and is sufficiently stable to survive the trip and remain within the sentinel node long enough to be detected. Magnetic or paramagnetic marking agents of the invention are preferably about 10 to about 200 nanometers in diameter. Magnetic or paramagnetic marking agents and pharmaceutically acceptable compositions containing them are generally disclosed in, e.g., U.S. Pat. Nos. 5,776,094, 5,582,172 and 5,101,827, and the references cited therein. Particularly preferred are compositions containing 10 to 200 nanometer iron, ferrite, gadolinium or other ferromagnetic, paramagnetic or magnetic resonance marking agent particles, which migrate to lymphatics when injected in the periphery of the tumor.

Magnetic resonance imaging probes and coils can provide an image of the sentinel lymph node in the context of an image of the adjacent blood vessels, a critical improvement over gamma detecting probes which only indicate the direction in which labeled tissue may be found by careful tissue dissection. Embodiments of the magnetic resonance detection systems of the invention comprise a transducer coil, signal processing electronics, reporting devices, and a power source.

Metal detecting and para-magnetic contrast agent detecting probes avoid patient and staff exposure to potentially harmful doses of ionizing radiation. Avoiding radioactive isotopes also avoids environmental contamination and disposal issues.

Detection Using Ultraviolet, Visible and Infrared Wavelengths, Including Monochromatic Laser Illumination Sentinel node localization can also proceed using ultraviolet, visible or infrared light illumination, complementary marking agents and complementary visualization means. The patient can be irradiated with ultraviolet, visible and/or infrared light subcutaneously injected or transcutaneously transmitted. The light source can be, e.g., a monochromatic laser, whose wavelength is dictated by the nature of the marking agent. The detection of reflected or fluorescing light with the naked eye and/or electronic imaging means noninvasively identifies the sentinel node without the need for pre-localization surgical dissection.

A marking composition comprising a marking agent is subcutaneously injected adjacent the tumor-bearing tissue and allowed sufficient time to migrate to the sentinel node before detection begins. The marking composition is preferably injected according to the European Institute of Oncology protocol between the skin and the immediately underlying tumor, or according to the National Cancer Institute protocol whereby 1 ml volumes of lymphatic tracer are injected at 3-, 6-, 9-, and 12-o'clock positions into the breast surrounding the primary tumor or biopsy cavity.

The marking composition is preferably a pharmaceutically acceptable composition containing marking agent and a carrier suitable for subcutaneous injection. The marking agent is sufficiently small to migrate from the tumor-bearing tissue to the sentinel node, and is sufficiently stable to survive the trip and remain within the sentinel node long enough to be detected. Marking agents of the invention are preferably about 10 to about 200 nanometers in diameter. Suitable marking agents include, e.g., lymphazurin blue dye, colloidal carbon particles, lymphazurin blue dye filled liposomes, other dye filled liposomes, dye containing colloids and dye containing microspheres, preferably coated with a phagocytosis enhancing material, such as tufsin.

Human or electronic observation can be through a disposable low resolution rigid penetrable fiberoptic device, with $\frac{1}{16}$" central fibers occupying $\frac{3}{8}$", and $\frac{1}{8}$" peripheral fibers occupying the remainder of the visualization field. However, the sentinel node and its signal can be detected without the use of fiberoptics. Embodiments of the detection systems of the invention comprise a light source (preferably a laser) that emits infrared, visible, ultraviolet and/or other light, a light sensor, signal processing electronics, reporting devices and a power source.

While the invention has been described in detail and with reference to specific examples thereof, it will be apparent to one skilled in the art that various changes and modifications can be made therein without departing from the spirit and scope thereof.

What is claimed is:

1. A method for identifying a sentinel node, comprising:
   injecting tumor-bearing tissue with a marking composition comprising a marking agent;

radiating marking-agent-targeting energy into suspect tissues potentially harboring said sentinel node; and detecting a lymph node first infiltrated by said marking agent to identify said sentinel node, said detecting being across a substantial thickness of said suspect tissues, wherein said method is conducted without detecting radioactivity.

2. The method of claim 1, wherein said substantial thickness of said suspect tissues is at least 2 mm.

3. The method of claim 1, wherein said substantial thickness of said suspect tissues is at least 5 mm.

4. The method of claim 1, wherein said marking agent comprises an ultrasound contrast agent, said energy comprises sound waves, and said detecting is conducted with an ultrasound probe.

5. The method of claim 4, wherein said ultrasound probe is non-imaging.

6. The method of claim 5, wherein said ultrasound probe is tissue-penetrable.

7. The method of claim 4, wherein said ultrasound probe is imaging.

8. The method of claim 7, wherein said ultrasound probe is tissue-penetrable.

9. The method of claim 4, wherein said ultrasound probe is adapted for both imaging and local signal intensity measurement.

10. The method of claim 9, wherein said ultrasound probe is tissue-penetrable.

11. The method of claim 1, wherein more than one said sentinel node is identified by detecting a plurality of lymph nodes first infiltrated by said marking agent.

12. The method of claim 1, wherein said marking agent comprises a magnetic or para-magnetic contrast agent, said energy comprises radiofrequency electromagnetic waves and said detecting comprises analyzing variations in magnetic or paramagnetic signal strength.

13. The method of claim 12, wherein said marking agent comprises 10 to 200 nanometer iron, ferrite or gadolinium particles.

14. The method of claim 12, wherein at least one of diamagnetism, paramagnetism, ferromagnetism, ferrimagnetism and antiferromagnetism is analyzed by a device comprising a transducer coil, signal processing electronics, reporting devices and a power source.

15. The method of claim 1, wherein said marking agent comprises a visible, infrared or ultraviolet light emitting, absorbing or reflecting agent, and said energy comprises a laser beam of visible, infrared or ultraviolet light.

16. The method of claim 15, wherein said sentinel node is detected with an ultraviolet, visible, or infrared transducer coupled to a sterile probe drape sheath.

17. The method of claim 1, wherein said marking composition comprises:

(a) a visible, infrared or ultraviolet light emitting, absorbing or reflecting agent as a first said marking agent, and (b) an ultrasound contrast agent as a second said marking agent, and said marking-agent-targeting energy comprises light and sound waves.

18. The method of claim 17, wherein the first said marking agent is a blue dye, said blue dye being visually detected in conjunction with an ultrasonic detection of the second said marking agent.

19. The method of claim 18, wherein the blue dye is lymphazurin blue.

20. An apparatus adapted to perform the method of claim 1, said apparatus comprising an energy radiating device and a detector.

21. The apparatus of claim 20, wherein said energy radiating device is selected from the group consisting of a piezoelectric ultrasound transmitting crystal, a piezoelectric ultrasound transmitting ceramic element, an electromagnetic energy transmitting coil, a radiofrequency transmitting coil, an ultraviolet laser, a visible laser, and an infrared laser.

22. The apparatus of claim 20, further comprising a sterile probe drape sheath.

23. The apparatus of claim 20, wherein said detector is disposable.

24. The apparatus of claim 20, wherein said energy radiating device is a radiofrequency generating transducer coil, and said detector is a magnetic resonance detecting coil.

25. The apparatus of claim 20, wherein said energy radiating device is an ultrasonic wave generator and said detector is an ultrasonic sensor.

26. The apparatus of claim 20, wherein said energy radiating device is a laser and said detector is a light sensor.

27. An apparatus adapted to perform the method of claim 1, said apparatus comprising a transducer coil adapted to carry out at least one of: (i) generation of a radiofrequency magnetic field and (ii) reception of magnetic or paramagnetic signal strength.

28. The apparatus of claim 27, adapted to analyze at least one of diamagnetism, paramagnetism, ferromagnetism, ferrimagnetism and antiferromagnetism.

29. A marking composition adapted for use in the method of claim 1, comprising marking agent particles coated with a phagocytosis enhancing material, wherein said marking agent particles have a diameter of about 10 to about 200 nanometers.

30. The marking composition of claim 29, wherein said marking agent particles are ultrasound contrast agents.

31. The marking composition of claim 29, wherein said marking agent particles are magnetic or para-magnetic contrast agents.

32. The marking composition of claim 29, wherein said marking agent particles are iron, ferrite or gadolinium.

33. The marking composition of claim 29, wherein said marking agent particles are visible, infrared or ultraviolet light emitting, absorbing or reflecting agents.

34. A system for identifying a sentinel lymph node in a living being, said system comprising:

means for introducing a marker composition substantially free of radioactive isotopes adjacent a suspected tumor site within said living being to enable a marker in said marker composition to be carried by the lymphatic system to a lymph node; and detection means adjacent the body of the living being, for detecting said sentinel lymph node into which said marker first infiltrates, said detection means being adapted to detect said sentinel node across a substantial thickness of tissue.

35. The system of claim 34, wherein said detection means detects non-visible electromagnetic radiation or ultrasound. lymphazurin blue.

* * * * *